United States Patent
Wang et al.

(10) Patent No.: US 12,251,162 B2
(45) Date of Patent: Mar. 18, 2025

(54) BENDING MECHANISM AND SURGICAL ROBOTIC ARM INCLUDING THE SAME

(71) Applicant: Sichuan Cancer Hospital & Institute, Chengdu (CN)

(72) Inventors: Xiangfei Wang, Chengdu (CN); Yu Wang, Chengdu (CN); Jiahua Lv, Chengdu (CN); Hailie Li, Chengdu (CN)

(73) Assignee: Sichuan Cancer Hospital & Institute, Chengdu (CN)

( * ) Notice: Subject to any disclaimer, the term of this patent is extended or adjusted under 35 U.S.C. 154(b) by 0 days.

(21) Appl. No.: 18/930,511

(22) Filed: Oct. 29, 2024

(65) Prior Publication Data
US 2025/0049503 A1    Feb. 13, 2025

Related U.S. Application Data (63) Continuation of application No. PCT/CN2023/095225, filed on May 19, 2023.

(30) Foreign Application Priority Data

May 31, 2022 (CN) .......................... 202210616161.8

(51) Int. Cl.
   *A61B 34/00* (2016.01)
   *A61B 34/30* (2016.01)

(52) U.S. Cl.
   CPC ........ *A61B 34/00* (2016.02); *A61B 2034/302* (2016.02)

(58) Field of Classification Search
   CPC ......... A61B 1/0055; A61B 1/008; A61B 1/01; A61B 1/018; A61B 2034/301;
   (Continued)

(56) References Cited

U.S. PATENT DOCUMENTS

| 7,971,504 B2 | 7/2011 | Haniya et al. |
| 11,130,244 B2 | 9/2021 | Jogasaki et al. |

(Continued)

FOREIGN PATENT DOCUMENTS

| CN | 101272886 A | 9/2008 |
| CN | 106891330 A | 6/2017 |

(Continued)

OTHER PUBLICATIONS

International Search Report, International Appl. No. PCT/CN2023/095225, Aug. 25, 2023, issued by the China National Intellectual Property Administration (ISA/CN), Beijing, China.

(Continued)

*Primary Examiner* — Scott Luan
(74) *Attorney, Agent, or Firm* — Andrew D. Fortney; Central California IP Group, P.C.

(57) ABSTRACT

The disclosure particularly relates to a bending mechanism and a surgical robotic arm including this mechanism. bending mechanism includes a flexible shell and a plurality of bending modules, arranged serially or in front-to-back connection. The bending modules are housed within the flexible shell. The bending modules include an adjustment drive assembly, a first adjustment shaft, and a second adjustment shaft. The first adjustment shaft and the second adjustment shaft are movably connected through a connecting part, the adjusting drive assembly is connected with the first adjustment shaft and the second adjustment shaft, and the adjusting drive assembly is configured to adjust an angle between the first adjustment shaft and the second adjustment shaft. The bending mechanism and surgical robotic arm aim to solve problems concerning damage caused to the human body.

9 Claims, 4 Drawing Sheets (58) Field of Classification Search
CPC .... A61B 2034/306; A61B 34/30; B25J 17/00; B25J 18/06; B25J 9/065; B25J 9/104; G06K 7/0008; G06K 7/10356
See application file for complete search history.

(56) References Cited

U.S. PATENT DOCUMENTS

| | | |
|---|---|---|
| 2003/0135204 A1 | 7/2003 | Endo |
| 2009/0114052 A1 | 5/2009 | Haniya et al. |
| 2017/0014998 A1 | 1/2017 | Langenfeld et al. |

FOREIGN PATENT DOCUMENTS

| | | |
|---|---|---|
| CN | 111482949 A | 8/2020 |
| CN | 112545654 A | 3/2021 |
| CN | 113442164 A | 9/2021 |
| CN | 113598949 A | 11/2021 |

OTHER PUBLICATIONS

Search Report and Office Action, CN Appl. No. 202210616161.8, dated Jun. 28-29, 2023; China National Intellectual Property Administration, Beijing, China.

Notification to Grant Patent Right for Invention, CN Appl. No. 202210616161.8, dated Aug. 31, 2023; China National Intellectual Property Administration, Beijing, China.

BENDING MECHANISM AND SURGICAL ROBOTIC ARM INCLUDING THE SAME

RELATED APPLICATION(S)

This application is a continuation of International Pat. Appl. No. PCT/CN2023/095225, filed on May 19, 2023, pending, which claims the benefit of Chinese Pat. Appl. No. 202210616161.8, filed on May 31, 2022 in the National Intellectual Property Administration, PRC (CNIPA), both of which are incorporated herein by reference.

TECHNICAL FIELD

The invention belongs to the medical field, and particularly relates to a bending mechanism and a surgical robotic arm including this mechanism.

BACKGROUND

Modern medical materials are often used to examine, sample or apply medicine inside of the body. In the prior art, in order to accomplish the above-described operation, surgery is often required (i.e., by cutting a specific part to expose the part to be treated, ultimately realizing examination, sampling, or application of medicine, etc.). The above-mentioned treatment methods can have a good therapeutic effect on healthy adults, but for special groups such as the elderly or children, the above-mentioned treatment methods are life-threatening.

In order to solve the above problems, some minimally invasive surgical devices have begun to appear in the prior art. The minimally invasive surgical devices can directly enter the human body through a natural channel (such as intestinal tract) or an artificial channel (such as a stoma channel) on the human body, and then operate on the human body. However, due to the complex situation in the human body, when the existing minimally invasive surgical devices work in the human body, the minimally invasive surgical devices can usually only perform passive bending or small bending. Therefore, existing minimally invasive surgical devices may cause damage to the internal tissues of the human body.

SUMMARY

The invention provides a bending mechanism and a surgical robotic arm including this mechanism, aiming at solving the problem of damage caused to a human body by minimally invasive surgical devices in the prior art.

In order to achieve the above object, the present invention provides a bending mechanism comprising a flexible shell and a plurality of bending modules connected sequentially or in series, where the bending modules are in the flexible shell.

Each bending module includes an adjustment drive assembly, a first adjustment shaft and a second adjustment shaft, wherein the first adjustment shaft and the second adjustment shaft are movably connected through a connecting part, the adjustment drive assembly is connected with the first adjustment shaft and the second adjustment shaft, and the adjustment drive assembly is configured to drive an angle change between the first adjustment shaft and the second adjustment shaft.

The invention includes a plurality of connected bending modules, and the bending modules can be substantially freely bent. The bending modules can avoid vital organs in the body by bending, and reduce or avoid damage to internal organs of the patient.

The bending modules can flexibly bend in the body to avoid compression on the internal tissues of the body.

Further, in order to realize multi-directional bending of the bending modules, the bending modules may include a plurality of adjustment drive parts or pieces, and the adjustment drive parts at different positions may be arranged symmetrically around the connecting part. The adjustment drive parts at different positions are configured to drive the first adjustment shaft in different directions (e.g., in a plurality of directions in each of one or two Cartesian dimensions).

When it is necessary to drive or bend the bending modules in different directions, the adjustment drive assembly can be operated in different directions, thereby adjusting and/or offsetting the bending modules in different directions.

Further, in one of the present aspects, the adjustment drive assembly preferably includes four symmetrical drive parts or pieces around the connecting part.

The adjustment drive assembly is preferably arranged in four symmetrical directions (e.g., in a plane) around the connecting part. When it is necessary to adjust the bending module to any side, the bending requirement of the bending module can be met by the mutual cooperation of the adjusting drive assemblies in the four directions.

Further, in order to change of the angle of the first adjustment shaft (e.g., relative to the second adjustment shaft), the adjustment drive assembly according to the present aspect includes one or more drive motors and an adjustment part. The drive motor is on the connecting part or a corresponding bearing, and the adjustment part is connected to the second adjustment shaft.

The adjustment part is arc-shaped, and the inner surface includes teeth. The drive motor includes a gear that meshes with the teeth.

The drive motor and the adjustment part are respectively located on and/or affixed directly or indirectly to the connecting part and the second adjustment shaft, respectively, in one embodiment. When the drive motor drives the adjustment part to move (e.g., through rotation of the gear meshed with the adjustment part), the adjustment part can drive (e.g., change the angle of) the second adjustment shaft (e.g., toward or away from the mounting side of the drive motor), and finally realize the angle change of the first adjustment shaft and/or the second adjustment shaft.

Further, in order to ensure that the bearing can still fit tightly with the adjustment part after the tilting of the adjustment part. The drive motor is connected to the connecting part through a bearing. The bearing has an inner ring and an outer ring, and the connecting part and the drive motor are respectively mounted on the inner ring and the outer ring.

When the adjustment part is tilted, the drive motor passively rotates on the bearing, so that the gear at the output end of the drive motor and the connecting part are always matching, and the adjustment part avoids getting stuck on the bearing after the adjustment part is tilted.

Further, in order to avoid the bending modules being hindered by the flexible shell when bending; the bending modules are in the middle of the flexible shell, and the bending modules and the flexible shell are fixedly connected by one or more supporting parts.

By providing the supporting part(s) to support the bending modules, the bending modules can bend the flexible shell accordingly when bending. Because of the supporting part (s), there is a gap between each of the bending modules and the flexible shell, and the flexible shell avoids interfering with the movement of the bending modules.

Further, in order to avoid damage to the bending modules, and at the same time, enabling the bending modules to be bent more flexibly, pressure sensors are uniformly arranged or distributed on the supporting part(s), and the pressure sensors sense the pressure on or received by different sides of the flexible shell.

The pressure sensors determine the pressure on different sides of the bending module, so that the bending module can move (e.g., one or both of the adjustment shafts) toward the opposite side (e.g., the side of the flexible shell having the lower pressure).

The invention also provides a minimally invasive surgical mechanical arm, comprising the above-mentioned bending mechanism, a head and a tail, wherein the head and the tail are respectively at opposite ends of the bending mechanism, and the head is equipped with a medical tool.

Both the head and the bending mechanism are configured to enter the human body. When the bending mechanism enters the human body, the bending mechanism can be bent so that the bending mechanism and the medical tool avoid organs in the human body.

Further, in order to realize the exchange of substances in vivo and in vitro, the present embodiment further includes one or more connecting channels, and the connecting channel(s) extend from the tail to the head.

By providing the connecting channel(s), medicine or gas can be delivered to the body through one connecting channel, and the accumulated fluid in the body can be discharged to the outside through the same or different connecting channel.

Further, the mechanical arm may be prevented from damaging the human body in the process of entering the human body. For example, a puncture needle may puncture the trachea inside the human body and the skin overlying the trachea. The head has a cross-sectional area enabling it to enter the body through such a puncture. The medical tool is in the head of the mechanical arm, and the head may include a moving mechanism, and the moving mechanism is configured to drive the medical tool to extend outside the head and retract back inside the head.

When the present mechanical arm enters the human body, the medical tool is in the head, but does not protrude or extend from the head, thereby avoiding damage to the human body. The medical tool is driven by a moving mechanism. When the head of the mechanical arm reaches the predetermined position, the moving mechanism drives the medical tool to extend from the head, and when the medical tool is not in use, the moving mechanism may retract the medical tool into the head.

The invention has the beneficial effect that the present bending modules can be bent. When the bending modules reach the body, the bending modules can avoid organs and tissues in the body by bending, thereby avoiding damage to the organs and/or tissues.

The reference numerals in the Figures include: a flexible shell 1, a bending module 2, an adjustment drive assembly 21, a drive motor 211, an adjustment part 212, a gear 213, a first adjustment shaft 22, a second adjustment shaft 23, a connecting part 24, a bearing 25, a supporting part 3, a head 4, a medical tool 401, a moving mechanism 402, a tail 5, and a connecting channel 6.

DETAILED DESCRIPTION

In order to make the objects, technical solutions, and advantages of the embodiments more clearly understood, the present invention is described in further detail below with reference to the accompanying drawings and examples. It is to be understood that the specific embodiments described herein are intended to illustrate the invention only and are not intended to limit the invention.

One or more first embodiments are basically as shown in FIGS. 1 to 6. A bending mechanism includes a flexible shell 1 and bending modules 2, and the bending modules 2 are in the flexible shell 1. When the bending modules 2 bend, the flexible shell 1 is bent accordingly. In the present embodiment, a plurality of bending modules 2 are provided, and the bending modules 2 are connected to each other serially (e.g., in the front and rear directions). Each bending module 2 can be bent within a small angular range, but the plurality of bending modules 2 can be bent in the same or different directions at the same time, so that the entire mechanical arm can be bent in different directions.

The number of bending modules 2 (and/or the lengths of the first and second adjustment shafts 22 and 23) correspond to the depth to which the mechanical arm enters the human body. The plurality of bending modules 2 are present if it is necessary to enter a deeper part of the human body to perform work.

The flexible shell 1 in the first embodiment(s) is specifically a metal hose, a rubber hose, a silicone hose, or the like provided with a hard layer inside. If the flexible shell 1 is a metal hose, the surface of the flexible shell 1 needs to be provided with a rubber layer or a silica gel layer. The flexible shell 1 directly contacts the human body, but the flexible shell 1 does not need to be relatively soft.

In one or more embodiments, the bending module 2 specifically includes an adjustment drive assembly 21, a first adjustment shaft 22, and a second adjustment shaft 23. Both the first adjustment shaft 22 and the second adjustment shaft 23 are hard shaft bodies, for example, metal shafts or the like. The first adjustment shaft 22 and the second adjustment shaft 23 are movably connected by a connecting part 24, and the first adjustment shaft 22 and the second adjustment shaft 23 are movably rotatable about the connecting part 24, thereby enabling the first adjustment shaft 22 and the second adjustment shaft 23 to have an adjustable angle between them. The adjustment drive assembly 21 is between the first adjustment shaft 22 and the second adjustment shaft 23, and is configured to drive an angular change between the first adjustment shaft 22 and the second adjustment shaft 23.

In the present embodiment(s), the bending module 2 is connected to adjacent bending module(s) from the front to the rear (and vice versa). The second adjustment shaft 23 of an upstream or previous bending module 2 may be (or is connected to or integrated with) the first adjustment shaft 22 of the immediately downstream or subsequent bending module 2, and thereafter, and so on.

It should be noted that when the angle between the first adjustment shaft 22 and the second adjustment shaft 23 changes, the bending module 2 is connected to the front and rear, and finally the entire robot arm is bent.

In one embodiment, there are preferably four adjustment drive assemblies 21 in each bending module 2, and they are symmetrically arranged around the connecting part 24. The four adjustment drive assemblies 21 are configured to adjust the second adjustment shaft 23 (or the angle thereof with respect to the first adjustment shaft 22) in different directions, respectively, so that the entire bending mechanism can be flexibly turned.

It is preferable that the four adjustment drive assemblies 21 do not operate simultaneously. When it is necessary to move the second adjustment shaft 23 in a specific direction (e.g., along a plane of an adjustment part 212), it is only necessary for the adjustment drive assembly 21 corresponding to that direction to move the corresponding adjustment part 212, and ultimately shift the second adjustment shaft 23 in the desired direction. However, when the direction of the second adjustment shaft 23 is between adjacent adjustment drive assemblies 21 (e.g., not along a plane of an adjustment part 212), the adjacent adjustment drive assemblies 21 can be operated sequentially or simultaneously to complete the adjustment (e.g., in each of two dimensions).

In another embodiment, two adjustment drive assemblies 21 may be provided, so that the adjustment drive assembly 21 may bend the second adjustment shaft 23 in a direction along a single dimension (e.g., along the plane of the adjustment part 212).

The connecting part 24 in one or more embodiments is an axial joint or bearing, such as a ball joint, and the first adjustment shaft 22 and the second adjustment shaft 23 are respectively connected through the ball joint 24. The connecting part 24 includes the ball at one end of the second adjustment shaft 23 and the spherical socket at a corresponding end of the first adjustment shaft 22, surrounding the ball at the end of the second adjustment shaft 23. The first adjustment shaft 22 and the second adjustment shaft 23 can rotate about the ball joint 24.

In order to make the angle at which the second adjustment shaft 23 can be adjusted larger, the socket of the ball joint 24 at end of the first adjustment shaft 22 may be much larger than the ball at the end of the second adjustment shaft 23.

In this aspect, the adjustment drive assembly 21 includes a drive motor 211 and an adjustment part 212. The adjustment part 212 is connected or affixed to the second adjustment shaft 23, and the adjustment part 212 may comprise an adjustment rod, which may be curved and which may comprise a metal or metal alloy. The adjustment part 212 may have an arc shape as a whole, and its inner surface may comprise teeth that mesh with a gear 213. The drive motor 211 is on the outer surface of the ball joint. At the same time, the output end of the drive motor 211 includes the gear 213. In the present embodiment(s), the gear 213 meshes with the teeth of the adjustment part 212. When the drive motor 211 rotates, the gear 213 transmits a force to the teeth, thereby causing the adjustment part 212 to move. When the adjustment part 212 moves, the second adjustment shaft 23 rotates, and finally the angle between the first adjustment shaft 22 and the second adjustment shaft 23 changes.

In one embodiment, the output end of the drive motor 211 may be provided with a limiting part, and the limiting part may include the connecting part 24 and/or a limiting roller (not shown). The limiting roller and the teeth of the gear 213 are parallel to each other, and one or more ends of the limiting roller may be connected to the output shaft of the drive motor 211, optionally through the connecting part 24. The output shaft of the drive motor 211 and the connecting part 24 may be connected (e.g., rotatably) through a connecting hole. The connection hole may be in the connection part 24, and the output shaft may be inserted into the connection hole. The diameter of the connection hole is larger than the diameter of the output shaft. When the output shaft rotates, the connecting part 24 does not rotate accordingly. The distal end of the output shaft may also include a limiting protrusion for abutting the connecting part 24 (e.g., against the connecting part 24), thereby preventing the connecting part 24 from disengaging from the output shaft.

In this embodiment, the adjustment part 212 may be accommodated between the limit roller and the gear 213. Consequently, the limit roller and the gear 213 can cooperate with each other to restrict the range of motion of the adjustment part 212 and/or prevent the adjustment part 212 from disengaging from the gear 213, and ensure the stable operation of the adjustment part 212.

If the size of the motor 211 is too large, the motor may be on or adjacent to the side surface of the gear 213. After that, a follower gear 213 may be separately mounted on the motor, and the follower gear 213 meshes with the gear 213 on the output shaft of the motor. When transmission is performed, the gear 213 on the output shaft of the drive motor 211 can drive the follower gear 213 to rotate. The follower gear 213 also meshes with the teeth of the adjustment part 212, so that the adjustment part 212 is driven and moved.

The gear 213 on the output shaft in one embodiment can be replaced with two pinion gears 213 that mesh with each other. One of the two pinion gears 213 is on the output shaft, and the rotating shaft of the other gear 213 is fixed to or mounted on the shell of the drive motor 211, parallel to the output shaft. The two pinion gears 213 mesh with each other. When the gear 213 on the output shaft rotates, the pinion gear 213 meshing therewith rotates. The gear 213 connected to the shell of the drive motor 211 meshes with the adjustment part 212, so that the adjustment part 212 is driven to move, as shown in FIG. 3.

The drive motor 211 in the present embodiment(s) is connected to the connecting part 24 through a bearing 25. The drive motor 211 may be mounted or provided on an outer ring of the bearing 25, and the connecting part 24 may be connected to an inner ring of the bearing 25. Alternatively, the drive motor 211 may be mounted or provided on the inner ring of the bearing 25, and the connecting part 24 may be connected to the outer ring of the bearing 25. The drive motor 211 can rotate on the bearing 25.

It should be noted that since a plurality of adjustment drive assemblies 21 are present in the embodiment(s), and since the drive motor 211 drives the adjustment part 212 to rotate the second adjustment shaft 23, the angle and/or position of the adjustment shaft located on the other side (e.g., upstream) of the second adjustment shaft 23 will also change accordingly. Therefore, in order to allow the adjustment shaft to cooperate with the gear 213 at the output of the drive motor 211 after being driven, the drive motor 211 is connected to the connecting part 24 via the bearing 25.

Figure 1:
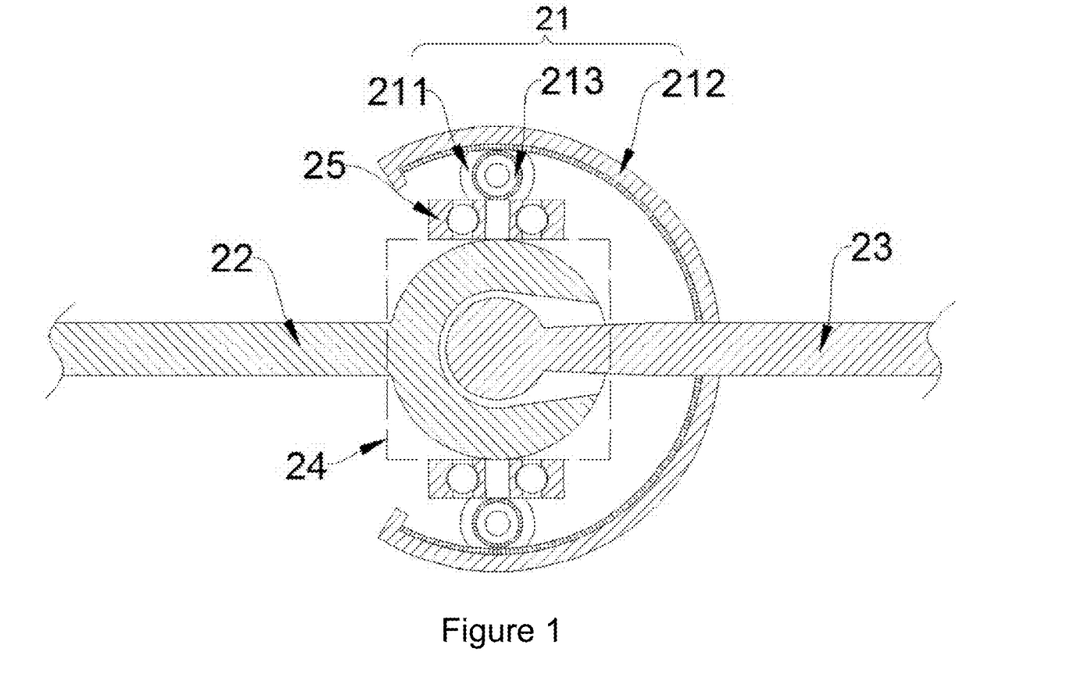
FIG. 1 is a schematic structural diagram of a bending module when it is not bent.
Figure 2:
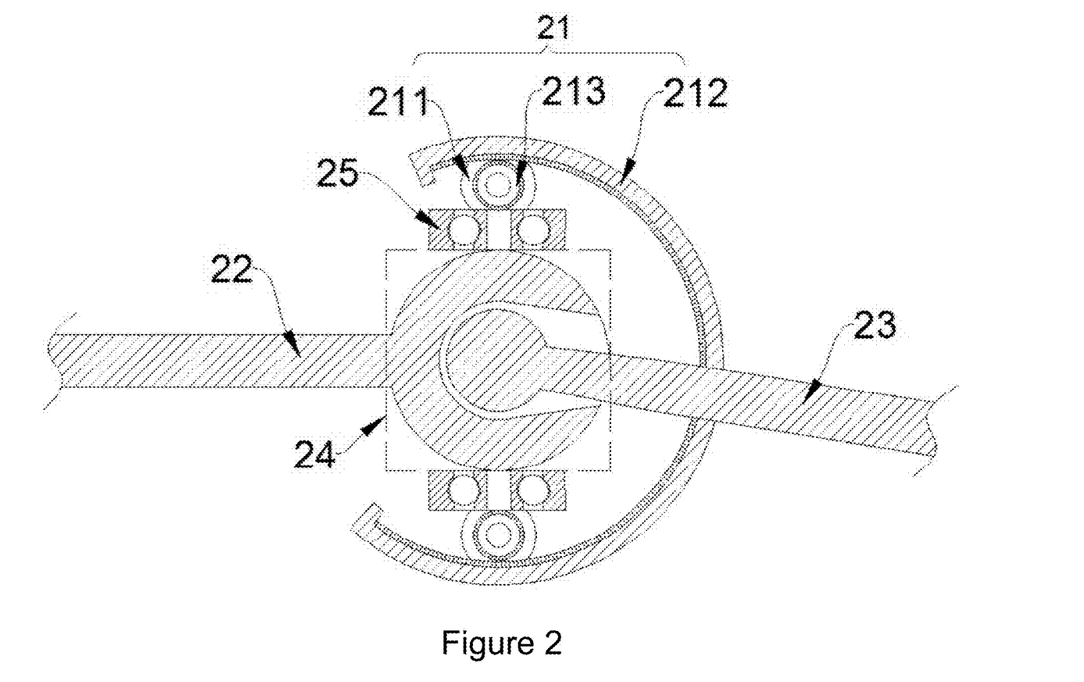
FIG. 2 is a schematic structural diagram of the bending module after bending.
Figure 3:
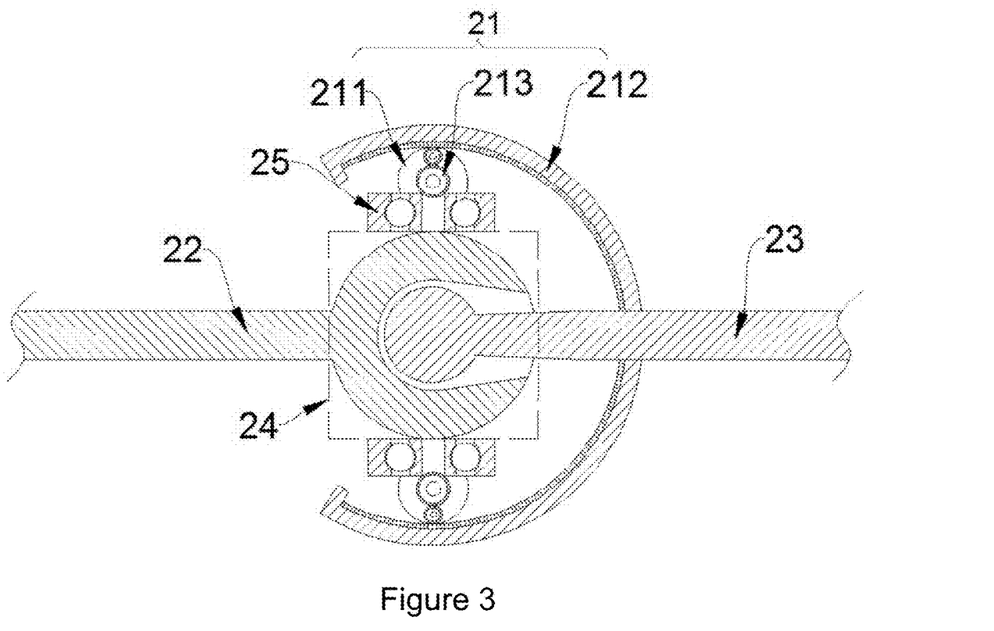
FIG. 3 is a schematic structural diagram of a bending module with a follower gear.

In one embodiment, the distal end of the adjustment part 212 is provided with a limiting portion, and the limiting portion may specifically be a limiting or stop bump (shown, but not identified, in FIGS. 1-3). When the gear 213 comes into contact with the stop bump, the stop bump can block further rotation of the gear 213, thereby preventing the adjustment part 212 from being disengaged from the gear 213.

The flexible shell 1 in the embodiment(s) may specifically be a hollow cylindrical pipe. The bending module 2 is in the middle of the pipe, and the bending module 2 and the pipe are connected by a supporting part 3. The supporting part 3 in one embodiment includes a circular portion and a supporting portion (shown, but not identified, in FIG. 6), and the circular portion may have a circular shape for matching with the inner wall of the pipe. The circular part is fixed or connected to the inner wall of the pipe. The supporting portion is specifically one or more supporting rods, and ends of the supporting rod(s) are respectively connected with the circular portion and the outer surface of the connecting part 24. The end of the support rod may also extend into the pipe material of the flexible shell 1, so that the connection between the supporting part 3 (e.g., the support rod) and the flexible shell 1 is more stable.

In one embodiment, pressure sensors may be on or in the circular portion. The pressure sensors may be distributed evenly around the circular portion to sense the pressure on different sides of the manipulator arm and/or the flexible shell 1.

It should be noted that when the pressure sensor on one side senses that the pressure exceeds a threshold value, the operator can instruct the mechanical arm to bend toward the opposite side using a control terminal, thereby avoiding damage to the mechanical arm due to excessive force. When the mechanical arm is in the human body, the control terminal can instruct the mechanical arm to bend in response to differential pressures detected by the pressure sensors (e.g., following the respiratory rate of the human body), so as to prevent the mechanical arm from being compressed and damaged by movement of the human body.

Figure 6:
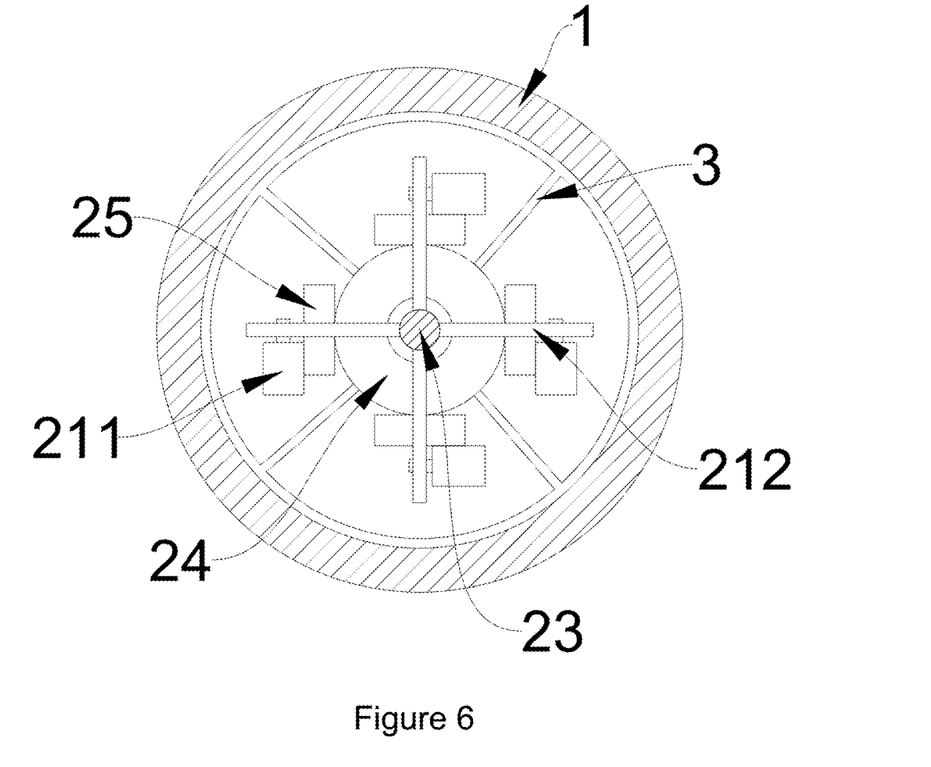
FIG. 6 is a cross-sectional view of the robot arm according to the first embodiment.

The circular portion of the supporting part 3 in the embodiment shown in FIG. 6 may be replaced by a V-shaped supporting part. One or more ends of the V-shaped supporting part are fixed or connected to the flexible shell 1, and the other end (e.g., the vertex) is connected to a support rod. The pressure sensor may be located in the middle (e.g., at the vertex) of the V-shaped supporting part.

In one embodiment, wiring is also present, and the wiring can be placed directly on the inner wall of the flexible shell 1, or along the first adjustment shaft 22 and the second adjustment shaft 23. The wiring is connected to each of the drive motors 211 and (when present) each of the pressure sensors, thereby enabling control outside the body of the operation of the drive motors 211 and the pressure sensors.

It should be noted that in this embodiment, the wiring is connected to an external control terminal. The control terminal is configured to control a specific bending direction of the mechanical arm (or of each adjustment drive assembly 21), and one or more of the motors 211 at one or more specific positions are activated or started, so that the bending mechanism can be moved in a specific direction. The control terminal may comprise a computer (e.g., a PC, laptop, tablet or industrial computer).

Figure 4:
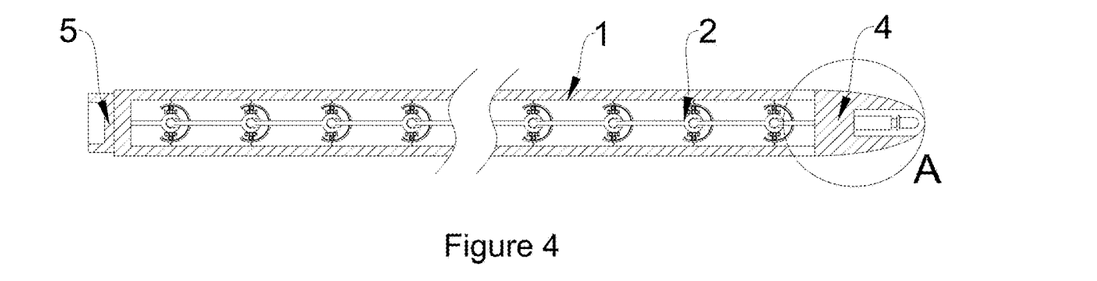
FIG. 4 is an overall schematic diagram of the robot arm according to a first embodiment.
Figure 5:
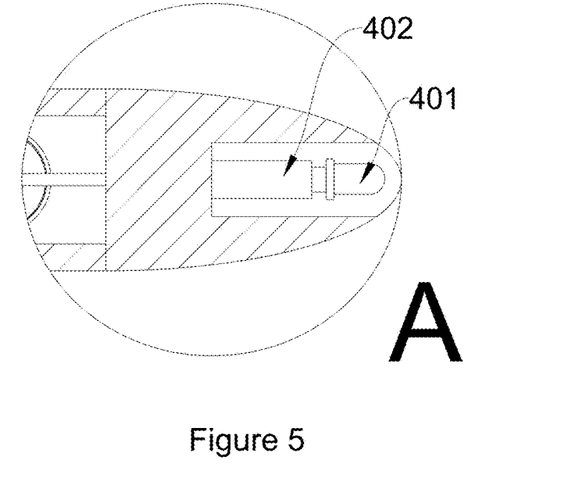
FIG. 5 is an enlarged view of part A in FIG. 4.
Figure 7:
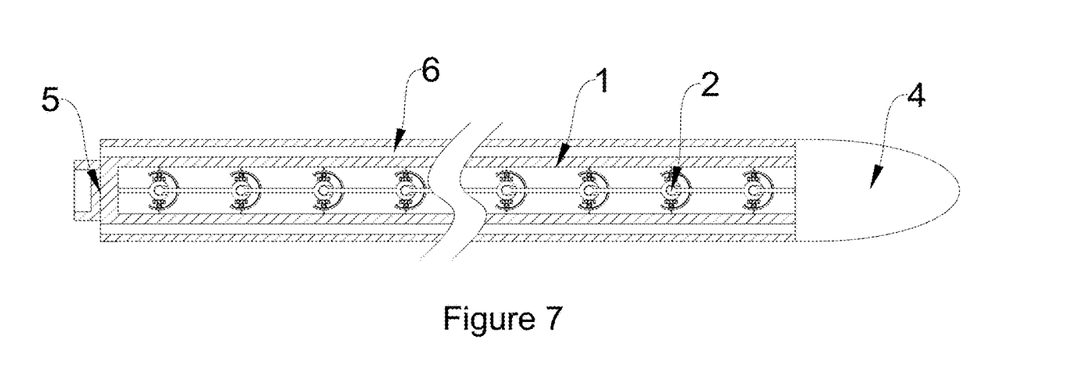
FIG. 7 is an overall schematic diagram of a robot arm according to a second embodiment.

The invention also provides a minimally invasive surgical mechanical arm, which includes the above-mentioned bending mechanism, a head 4 and a tail 5 (see, e.g., FIGS. 4 and 7). The head 4 and the tail 5 are at opposite ends of the bending mechanism.

The head 4 of the mechanical arm in the embodiment(s) enters the human body. The tail 5 of the mechanical arm includes an interface configured to connect with the mechanical arm or a conventional pushing mechanism, and the mechanical arm or the pushing mechanism can provide power for the head 4 to enter the human body.

In the present embodiment(s), the head 4 is configured to house and/or hold a medical tool 401. When the head 4 reaches a predetermined position in the body, the medical tool 401 can then be operated to treat the human body.

It should be noted that the mechanical arm in the present embodiment(s) may cooperate with an imaging device. The imaging device includes a source of irradiation so that the control terminal can image the path of the mechanical arm in the human body (e.g., its organ[s] and/or tissue[s]), so that the mechanical arm can accurately reach a predetermined position. At the same time, the mechanical arm can bend around the body organ, so as to avoid damage to the organ.

Since the mechanical arm in the present embodiment(s) enters the human body, the size of the mechanical arm should be small. However, when limited to the manufacturing and assembly processes in the prior art, the mechanical arm cannot meet the needs of some particularly narrow use scenarios.

In one embodiment, the medical tool 401 may be a sampling needle, a camera, a scalpel, a combination thereof, or the like. When the head 4 of the mechanical arm reaches the predetermined position, the medical tool 401 operates, thereby realizing the treatment of the human body.

When the medical tool 401 is a scalpel, the head 4 is further provided with a vibrator. A vibrator causes a scalpel to vibrate, thereby cutting specific parts of the body. Alternatively, bending the bending module 2 may also move the scalpel, thereby cutting human tissue.

In one embodiment, the head 4 of the mechanical arm includes a shell groove (shown, but not identified in FIG. 5), and the medical tool 401 is housed in the shell groove. The medical tool 401 does not protrude from the head 4, thereby preventing the mechanical arm from causing damage to the human body when entering the human body. A moving mechanism 402 is in the shell groove, and the moving mechanism 402 can extend the medical tool 401 from the shell groove, thereby ensuring the operation of the medical tool 401. The moving mechanism 402 in some embodiments may comprise a telescopic device (e.g., a piston) or a lead screw drive motor.

If the medical tool 401 includes a camera, the shell groove and the moving mechanism 402 may not be necessary because the camera generally does not cause injury to the human body.

Hereinafter, it will be described with reference to a specific embodiment that when it is necessary to perform surgery inside the human body, the mechanical arm can enter the human body under the action of an external mechanical arm or a pushing mechanism. When the mechanical arm enters the human body, the mechanical arm can be bent, thus avoiding vital organs in the body.

When the head 4 of the robot arm reaches the predetermined position, the medical tool 401 can be extended by the moving mechanism 402 to perform a medical operation. After use, the moving mechanism 402 can retract the medical tool 401 back into the shell groove in the head 4.

Example 2

Figure 8:
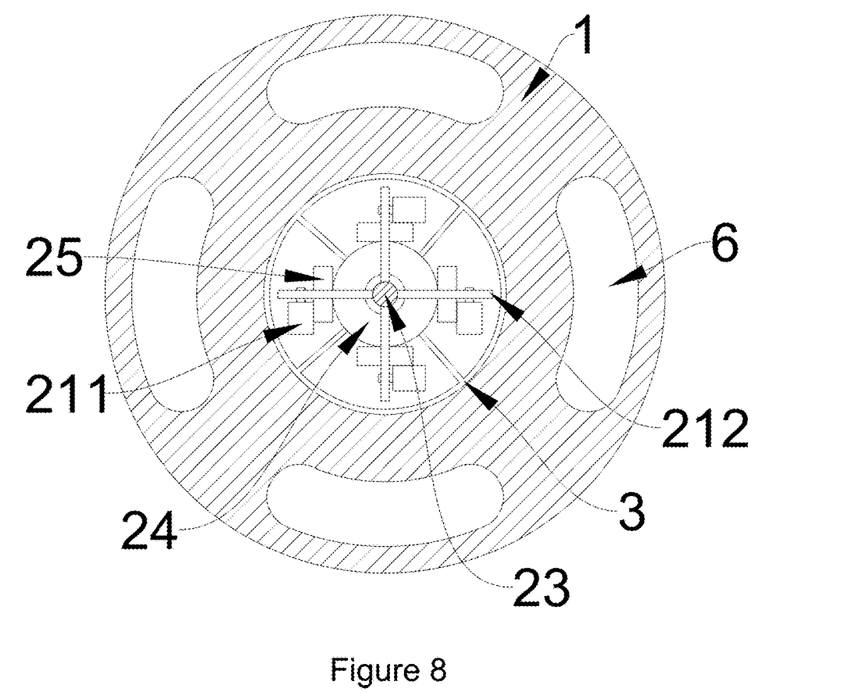
FIG. 8 is a cross-sectional view of the robot arm according to the second embodiment including connection channels in the flexible shell.
Figure 9:
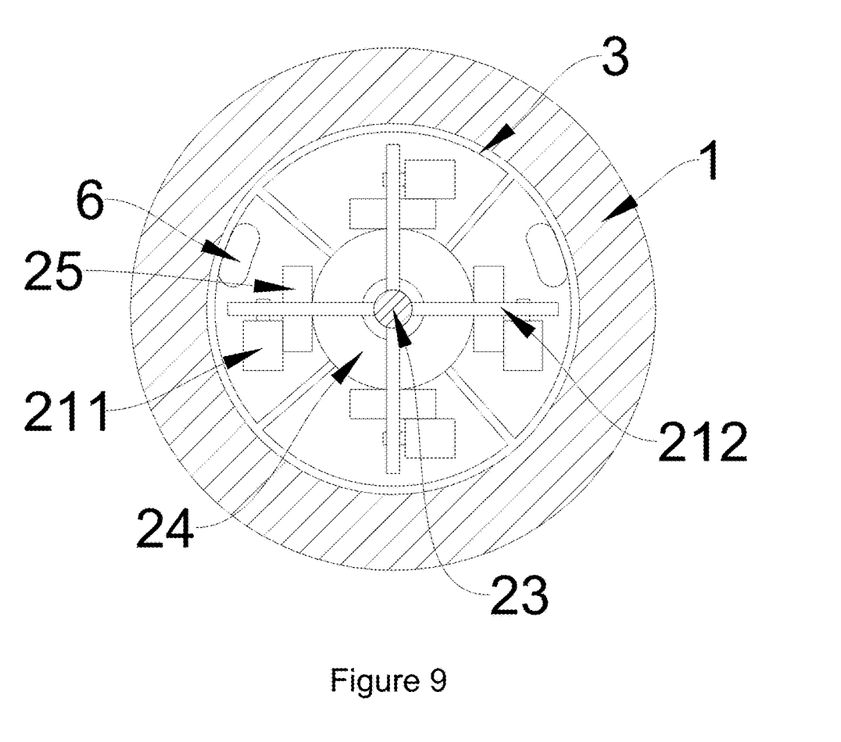
FIG. 9 is a cross-sectional view of the robot arm according to the second embodiment including connection channels between the curved module and the flexible shell.

The difference between this example and the above embodiment(s) is that, as shown in FIGS. 7 to 9, this example further includes a connecting channel 6, and the connecting channel 6 extends from the tail 5 into the head 4. The connecting channel 6 may be in communication with the medical tool 401. Through one or more of the connection channels 6, medicine or gas can be directly injected into the body from the outside. Alternatively, the accumulated fluid in the body may be drawn out of the body through one or more of the connection channels 6 (preferably different from those used for medicine or gas). In one embodiment, the medical tool 401 comprises a puncture needle or other medical tool 401 that enables substance exchange, delivery or withdrawal.

The connection channel 6 in the one embodiment may be inside the flexible shell 1. Alternatively, the connection channel 6 may be in the gap between the bending module 2 and the flexible shell 1. When the connection channel 6 is in the gap between the bending module 2 and the flexible shell 1, the connection channel 6 may comprise a connection pipe.

It should be noted that when the connection channel 6 is in the gap between the bending module 2 and the flexible shell 1, the size (e.g., diameter) of the entire mechanical arm is smaller, and more likely to satisfy certain specifications for use. However, the diameter of the connecting channel 6 may be smaller than that in the flexible shell 1. When the connection channel 6 is in the gap between the bending module 2 and the flexible shell 1, a fixing ring may be provided on the inner wall of the flexible shell 1 for supporting the connection channel 6.

The above description is merely of embodiments of the present invention, and common knowledge such as specific structures and characteristics that are well-known in the art are not described in detail herein. It should be pointed out that for those skilled in the art, some modifications and improvements can be made without departing from the structure of the present invention, which should also be regarded as the scope of protection of the present invention, and these will not affect the effect of the implementation of the present invention and the practicability of the patent. The scope of protection claimed in this application shall be subject to the contents of the claims, and the description of the specific embodiments and the like in the specification can be used to interpret the contents of the claims.

What is claimed is:

1. A bending mechanism, comprising a flexible shell and a plurality of bending modules, wherein:
    the plurality of bending modules are connected in series;
    the bending modules are housed within the flexible shell;
    each of the bending modules comprises an adjustment drive assembly, a first adjustment shaft and a second adjustment shaft;
    the first adjustment shaft and the second adjustment shaft are movably connected by a connecting part;
    the adjustment drive assembly is connected to the first adjustment shaft and the second adjustment shaft, and the adjustment drive assembly is configured to drive an angle change between the first adjustment shaft and the second adjustment shaft;
    the adjustment drive assembly comprises a drive motor on the connecting part and an adjustment part connected to the second adjustment shaft;
    the adjustment part has an arc shape and an inner surface provided with teeth; and
    the drive motor includes a gear that meshes with the teeth.

2. The bending mechanism according to claim 1, wherein the adjustment drive assembly comprises a plurality of parts or pieces and is symmetrically arranged around the connecting part; the adjustment drive assembly is arranged in a symmetrical manner with the connecting part as a center; and the adjustment drive assembly at different positions is configured to drive offset the first adjustment shaft in different directions.

3. The bending mechanism according to claim 2, wherein the adjustment drive assembly comprises four symmetrical pieces around the connecting part.

4. The bending mechanism according to claim 1, further comprising a bearing connecting the drive motor to the connecting part, wherein the bearing has an inner ring and an outer ring, and the connecting part and the drive motor are respectively mounted on the inner ring and the outer ring.

5. The bending mechanism according to claim 1, wherein the bending modules are in a middle of the flexible shell, and the bending modules and the flexible shell are fixedly connected by a supporting part.

6. The bending mechanism according to claim 5, further comprising pressure sensors uniformly arranged on the supporting part, wherein the pressure sensors sense pressures on different sides of the flexible shell.

7. A minimally invasive surgical mechanical arm comprising a bending mechanism as claimed in claim 1, a head and a tail; the head and the tail are respectively at opposite ends of the bending mechanism, and the head is equipped with a medical tool.

8. The minimally invasive surgical mechanical arm according to claim 7, further comprising a connecting channel extending from the tail to the head.

9. The minimally invasive surgical mechanical arm according to claim 7, wherein: the medical tool is in the head, and the head includes a moving mechanism configured to drive the medical tool in and out of the head.

* * * * *